United States Patent [19]

Lussling et al.

[11] 4,303,621

[45] Dec. 1, 1981

[54] PROCESS FOR THE RECOVERY OF METHIONINE AND POTASSIUM BICARBONATE

[75] Inventors: Theodor Lussling, Hanau; Klaus-Peter Müller, Braunschweig; Gerd Schreyer; Ferdinand Theissen, both of Hanau, all of Fed. Rep. of Germany

[73] Assignee: Deutsche Gold- und Silber-Scheideanstalt vormals Roessler, Frankfurt, Fed. Rep. of Germany

[21] Appl. No.: 930,012

[22] Filed: Aug. 1, 1978

Related U.S. Application Data

[63] Continuation-in-part of Ser. No. 574,084, May 2, 1975, abandoned.

[30] Foreign Application Priority Data

May 2, 1974 [DE] Fed. Rep. of Germany ....... 2421167

[51] Int. Cl.$^3$ .............................................. C01D 7/00
[52] U.S. Cl. .................................... 423/189; 423/422; 562/559
[58] Field of Search ................ 562/559; 423/209, 186, 423/189, 422

[56] References Cited

FOREIGN PATENT DOCUMENTS 2421167 11/1975 Fed. Rep. of Germany .

*Primary Examiner*—O. R. Vertiz
*Assistant Examiner*—Wayne A. Langel
*Attorney, Agent, or Firm*—Cushman, Darby & Cushman

[57] ABSTRACT

Methionine and potassium are recovered from the recycling solution of the potassium carbonate-methionine process by concentrating the mother liquor after the methionine precipitation and with cooling carbonating the mother liquor.

13 Claims, No Drawings

PROCESS FOR THE RECOVERY OF METHIONINE AND POTASSIUM BICARBONATE

CROSS-REFERENCE TO RELATED APPLICATIONS

This application is a continuation-in-part of U.S. application Ser. No. 574,084, filed May 2, 1975 now abandoned which is relied upon and incorporated by reference herein.

In German Pat. No. 1,906,405 and corresponding British Pat. No. 1,296,347 there is described a process for the production of methionine by saponification of 5-[2-methylmercaptoethyl] hydantoin with a recycling alkali carbonate solution. The entire disclosure of British Pat. No. 1,296,347 is hereby incorporated by reference and relied upon.

The British patent describes a process for the production of methionine by hydrolyzing 5-[2-methylmercaptoethyl] hydantoin at elevated temperature (e.g. 120° to 220° C., preferably from 140° to 180° C.) and pressure (usually slightly higher than the steam pressure at the temperature employed) with an aqueous solution of an alkali metal carbonate (e.g. sodium carbonate or potassium carbonate) and/or an alkali metal hydrogen carbonate (e.g. sodium bicarbonate or potassium bicarbonate) removing ammonia and carbon dioxide during hydrolysis and precipitating methionine from the solution with carbon dioxide on completion of hydrolysis and recycling the mother liquor containing alkali metal hydrogen carbonate to the hydrolysis reaction. As in all cyclic processes this process also requires removal of a portion of the recycling mixture so that the byproducts formed do not increase beyond the amount which can be tolerated.

However, since the removed recycling solution still contains valuable amounts of methionine and potassium (i.e. $K^+$) and since for environmental reasons these solutions cannot be discharged without upgrading, there must be recovered as high as possible a portion of the valuable substances contained therein. Recovery is also recommended so that there can be reduced to a minimum the chemical requirements of the subsequent plant for protection of the environment.

The separation of the methionine and the potassium now can take place in a simple manner if there is subjected to a carbonation, as the reaction solution, the solution which has been concentrated for return into the saponification process, or if a part of such concentrated solution is so employed; which concentrated solution is obtained by concentrating the filtrate after the separation of the methionine; and the methionine and potassium precipitated together as free methionine and potassium hydrogen carbonate (potassium bicarbonate) and filtered off from the mother liquor. Unfortunately the mixture of materials precipitated thereby has extremely poor filtration properties and also has a tendency to provide a very strongly variable sedimentation. While the potassium bicarbonate precipitates as the heavier and more rapidly sedimenting crystals, the methionine separates as very fine crystals which float up in eliminating the methionine and potassium from the solution with the carbon dioxide.

These properties make extremely difficult a degassing of the carbonated solutions so that the degassing is coupled in a significant manner with the solid material separation for example by centrifuging. However, there remains the tendency of the methionine obtained to foam up so that only thin and poorly dewatered solid cakes can be obtained.

This causes the economical separation of the solids to be questioned since a large number of centrifuges is necessary for small amounts of solids. A separate separation of potassium hydrogen carbonate and methionine is completely eliminated since it is almost impossible to separate the methionine, it may be there in the form of a smear.

This character of the methionine first depends upon the fact that it crystallizes only poorly from the viscous mother liquor and in finely divided form and upon the fact that the impurities within the mother liquor adhere to the crystal surfaces as a smeary material. This causes the poor dewatering, this is especially true the higher are the concentrations of the added mother liquors to be worked up.

The object of the invention is to develop a carbonation process according to which the potassium hydrogen carbonate and methionine are precipitated from the mother liquor by carbon dioxide under such conditions that an easily filterable crystallizate is formed. This crystallizate besides has substantially lost its flotation properties.

It has been found that the methionine and potassium can be recovered from the recycling solutions of the potassium carbonate-methionine process by carbonation in an easily filterable form if the mother liquors resulting after the separation of the main amount of methionine are concentrated and carbonated with cooling.

The mother liquors (e.g. in forming methionine by hydrolyzing 5-[2-methylmercaptoethyl]-hydantoin) which still contain about 50–80 grams of methionine and 60–100 grams of titratable potassium per liter after separation of the methionine, are concentrated to a concentration of at least 120 grams of titratable potassium per liter. Concentrations above 210 grams of titratable potassium per liter, however, lead to solutions that are extremely difficult to carbonate, since the viscosity of these solutions upon cooling is very high.

By titratable potassium is meant that potassium which is titrated in the presence of a glass electrode or a suitable indicator at pH 4.5 with a mineral acid, e.g., HCl or $H_2SO_4$. Thus the titratable potassium in the Examples is that which can be found using hydrochloric acid with bromothymol blue as an indicator. Other suitable indicators include methyl orange and methyl red.

The carbonation occurs at carbon dioxide pressures of 0.5–20 atmospheres absolute. Pressures of 2–11 atmospheres absolute are very well suited and especially preferred are pressures of 3–7 atmospheres absolute. Pure carbon dioxide can be used. In adding inert gas containing $CO_2$ the pressure is valid for the $CO_2$-partial pressure.

The carbonation can begin at a temperature of 120° C., but preferably at 70° C. or lower, e.g. 64° C. and ends preferably at 35° C. However, cooling can be carried out at lower temperatures to 20° C.

Both constant and variable carbon dioxide pressures can be employed. However, it is preferred to use a constant pressure during the entire cooling.

While under otherwise identical carbonation conditions the filtration properties hardly change in the range of 3–7 atmospheres absolute, these deteriorate at 11 atmospheres absolute and higher. At otherwise equal carbonation conditions a purer product precipitates at lower pressures than at higher pressures.

In order to be able to return into the process for producing methionine as much valuable material as possible, i.e. potassium hydrogen carbonate and methionine, it is recommended in conjunction with the first carbonation to include a renewed concentration of the resulting mother liquor and a renewed carbonization. The now again precipitating product to be sure shows not nearly as good a centrifuging performance.

If diluted solutions are added to begin with, there can also be carried out more than 2 concentration and carbonation steps.

It has also been found very favorable to allow the concentrated mother liquor to remain at the carbonation temperature for 5-60 minutes after charging the carbon dioxide and then for the first time to begin the cooling. In this time the solution equilibrium between gas, mother liquor and crystallizate is established.

The same establishment of equilibrium is attained during the cooling; if the cooling is carried out stepwise and between each temperature interval there is present a time of residence. The cooling should be undertaken in temperature intervals of 3°-20° C. under the carbon dioxide pressure, and after each cooling the supersaturation formed is dissipated by residence of the carbonated mother liquor at the respective temperature for 5-60 minutes, preferably 5-30 minutes.

In detail the process is as follows:

The carbonation, as has been said, is begun at temperatures of up to 120° C. preferably 70° C. Carbon dioxide is impressed until the desired carbonation pressure is attained. The heat development which occurs thereby can be removed by cooling, which, however, is not necessary if the beginning temperature is increased still higher. However, 120° C. should not be exceeded. After a residence time, which also is sufficient to produce the equilibrium between the gas pressure and solution at the carbonation temperature and to break down the supersaturation of the solution formed by the carbonation, cooling is carried out in the mentioned temperature intervals at the prevailing carbon dioxide pressure.

The cooling time essentially depends upon apparatus data such as volume to the exchange surface and the innate temperature difference between cooling water and solution to be cooled.* As stated above, after each temperature reduction a residence time is introduced in order to again break down the supersaturation.

* It is recommended to cool as short as possible.

Naturally the process can be carried out continuously if crystallization is carried out in two or more carbonation cascades connected together under carbonation conditions. The individual cascade steps differ at times according to the desired temperature break. Here also the residence time is so chosen that the supersaturation can be substantially broken down in the individual steps. Likewise for this purpose 5-60 minutes is sufficient.

Naturally there can also be used the first described discontinuous process without pauses. However, the results are not as good.

Unless otherwise indicated all parts and percentages are by weight.

The following examples illustrate the process. They were carried out with highly concentrated solutions, since precisely with these solutions it is substantially more difficult to produce properly centrifuged solids than with dilute solutions.

The starting materials used in the following examples were obtained from a process of preparing methionine by hydrolyzing 5-[2-methylmercaptoethyl]-hydantoin.

EXAMPLE 1

There was provided in a pressure container a solution to be carbonated. The solution contained 180 grams/liter of titratable potassium, 135 grams/liter of methionine, 8 grams/liter of non titratable potassium, 144 grams/liter sulphur containing byproducts besides other impurities found in the cyclic process. The carbonation-crystallization was begun at 70° C. and 6 atmospheres absolute carbon dioxide pressure. After reaching the $CO_2$ pressure of 6 atmospheres absolute carbonation was carried out for 20 minutes at this temperature. After this while maintaining the $CO_2$ pressure uniform cooling to 60° C. was carried out within 30 minutes and the mixture kept at this temperature for 15 minutes. Subsequently cooling to 50° C. was carried out in 30 minutes and again the cooling interrupted for 15 minutes. Then the mixture was cooled in an hour to 35° C. The solution had a pH of 8.3. In order to avoid foaming of the product in the carbonation reactor the $CO_2$ pressure of 6 atmospheres absolute was also maintained during the subsequent employing of the pressure container by applying $CO_2$ to the surface of the crystal sludge. The crystallizate thus produced a centrifuge capacity at a centrifuge factor of 500 kg/kg of 110 $kg/m^2h$, calculated on the dry cake.

EXAMPLE 2

A solution corresponding to that employed in Example 1 was carbonated at 50° C. at 6 atmospheres absolute $CO_2$ pressure to pH 8.3 and then cooled to 35° C. The centrifuge capacity at a centrifuge factor of 500 kg/kg was 50 $kg/m^2h$ calculated on the dry cake.

EXAMPLE 3

A solution corresponding to that employed in Example 1 after reaching the $CO_2$ pressure was after carbonated at 70° C. and 6 atmospheres absolute for 20 minutes. Then the solution was continuously cooled in 45 minutes to 60° C. in a further 45 minutes to 50° C. and in 60 minutes to 35° C. under carbonation conditions. The solution had a pH value of 8.3. The centrifuge capacity produced at a centrifuge factor of 500 kg/kg was 76 $kg/m^2h$ calculated on the dry cake.

EXAMPLE 4

A solution corresponding to that employed in Example 1 after reaching the $CO_2$ pressure was after carbonated at 70° C. and 6 atmospheres absolute $CO_2$ pressure for 30 minutes. Then under carbonation conditions cooling was uniformly carried out for 30 minutes:
  in 20 minutes cooled to 64° C.
  held at 64° C. for 15 minutes
  in 15 minutes cooled to 60° C.
  held at 60° C. for 15 minutes
  in 15 minutes cooled to 55° C.
  held at 55° C. for 15 minutes
  in 60 minutes cooled to 35° C.

The solution then had a pH of 8.2, the centrifuge capacity at a centrifuge factor of 500 kg/kg was 150 $kg/m^2h$ calculated on the dry cake.

EXAMPLE 5

The procedure was the same as in Example 4 with the difference that the carbonation pressure was 11 atmospheres absolute. The centrifuge capacity at the same centrifuge factor was 120 kg/m²h calculated on the dry cake.

EXAMPLE 6

The procedure was the same as in Example 4 with the difference that the carbonation pressure was 3 atmospheres absolute. The centrifuge capacity at the same centrifuge factor was 155 kg/m²h calculated on the dry cake.

EXAMPLE 7

A solution corresponding to that in Example 1 was carbonated at 35° C. and 6 atmospheres absolute carbon dioxide pressure at pH 8.2. The centrifuge capacity at the same centrifuge factor as previously set forth was 35 kg/m²h calculated on the dry cake.

The process can comprise, consist essentially of or consist of the steps set forth.

What is claimed is:

1. In a process for the recovery of methionine and potassium bicarbonate from the solution recycling in the process of forming methionine by hydrolyzing 5-[2-methyl-mercaptoethyl]-hydantoin with aqueous potassium carbonate to form a mother liquor and precipitating methionine formed with carbon dioxide, the improvement comprising concentrating the aqueous mother liquor after separtion of the precipitated methionine to a titratable potassium ion concentration of 120 grams per liter to 210 grams per liter, and then carbonating the concentrated mother liquor with carbon dioxide and lowering the temperature by cooling from a temperature of not over 120° C. during the carbonation to form an easily filterable crystallizate.

2. The process of claim 1, wherein the carbonation is carried out with carbon dioxide at 0.5–20 atmospheres absolute carbon dioxide pressure.

3. The process of claim 2, wherein the carbonation is carried out in cascading containers and the temperature intervals between adjacent containers is lowered progressively from 3°–20° C.

4. The process of claim 3, wherein the carbonation begins at 70° C.

5. The process of claim 4, wherein the carbonated mother liquor is kept at the carbonation temperature between the individual temperatures for 5–60 minutes.

6. The process of claim 2, wherein the carbon dioxide carbonation pressure is 1–10 atmospheres absolute.

7. The process of claim 6, wherein the carbon dioxide carbonation pressure is 3–7 atmospheres absolute.

8. The process of claim 2, wherein after addition of the carbon dioxide the concentrated mother liquor is kept at the carbonation pressure for 5–60 minutes.

9. The process of claim 8, wherein the carbonation is carried out in cascading containers and the temperature intervals between adjacent containers is lowered progressively from 3°–70° C.

10. The process of claim 2, wherein the initial temperature of carbonation is at least 70° C.

11. The process of claim 1, wherein the initial temperature of carbonation is at least 70° C.

12. The process of claim 11, wherein the cooling is to a temperature no higher than 70° C.

13. The process of claim 11, wherein the difference between the initial temperature of carbonation and the final temperature of cooling is at least 35° C.

* * * * *